United States Patent [19]

Berg

[11] Patent Number: 5,759,359
[45] Date of Patent: Jun. 2, 1998

[54] SEPARATION OF 2-BUTANOL FROM TERT.AMYL ALCOHOL BY AZEOTROPIC DISTILLATION

[76] Inventor: Lloyd Berg, 1314 S. 3rd Ave., Bozeman, Mont. 59715

[21] Appl. No.: 925,469

[22] Filed: Sep. 8, 1997

[51] Int. Cl.⁶ .................. B01D 3/36; C07C 29/82
[52] U.S. Cl. .................. 203/57; 203/60; 203/62; 203/68; 203/70; 568/913
[58] Field of Search ............... 203/57, 60, 68, 203/70, 62; 568/913

[56] References Cited

U.S. PATENT DOCUMENTS

| | | | |
|---|---|---|---|
| 2,485,694 | 10/1949 | Burchfield | 203/88 |
| 2,559,519 | 7/1951 | Smith et al. | 203/64 |
| 2,570,205 | 10/1951 | Carlson et al. | 568/913 |
| 2,575,243 | 11/1951 | Carlson et al. | 203/60 |
| 2,663,679 | 12/1953 | Drout, Jr. | 203/84 |
| 2,663,680 | 12/1953 | Robertson | 203/84 |
| 2,706,707 | 4/1955 | Morrell et al. | 203/57 |
| 4,693,787 | 9/1987 | Berg et al. | 568/913 |
| 4,693,788 | 9/1987 | Berg et al. | 568/913 |
| 4,756,803 | 7/1988 | Berg | 203/60 |
| 4,935,103 | 6/1990 | Berg et al. | 203/57 |

*Primary Examiner*—Virginia Manoharan

[57] ABSTRACT

2-Butanol cannot be separated from t-amyl alcohol by distillation or rectification because of the closeness of their boiling points. 2-Butanol is readily separated from t-amyl alcohol by azeotropic distillation. Effective agents are methyl acetate, ethyl propionate and octane.

2 Claims, No Drawings

SEPARATION OF 2-BUTANOL FROM TERT.AMYL ALCOHOL BY AZEOTROPIC DISTILLATION

FIELD OF THE INVENTION

This invention relates to a method of separating 2-butanol from tert.amyl alcohol by azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

2-Butanol and t-amyl alcohol boil two degrees apart and have a relative volatility of 1.2 which makes it difficult to separate them by conventional distillation or rectification. Table 2 shows that with an agent giving a relative volatility of 1.7, only twenty-four actual plates are required to get 99% purity compared to 61 plates for straight rectification.

TABLE 2

Theoretical and Actual Plates Required vs. Relative Volatility for 2-Butanol and t. Amyl Alcohol Separation

| Relative Volatility | Theoretical Plates Required At Total Reflux, 99% Purity | Actual Plates Required, 75% Efficiency |
|---|---|---|
| 1.22 | 46 | 61 |
| 1.4 | 26 | 35 |
| 1.5 | 22 | 30 |
| 1.7 | 18 | 24 |

OBJECTIVE OF THE INVENTION

The object of this invention is to provide a process or method of azeotropic distillation, that will enhance the relative volatility of 2-butanol and t.-amyl alcohol in their separation in a rectification column. It is a further object of this invention to identify effective azeotropic distillation agents that are stable and can be recycled.

SUMMARY OF THE INVENTION

The objects of this invention are provided by a process for the separation of 2-butanol and t.-amyl alcohol which entails the use of certain organic compounds when employed as the agent in azeotropic distillation.

DETAILED DESCRIPTION OF THE INVENTION

I have discovered that certain organic compounds will effectively increase the relative volatility between 2-butanol and tert. amyl alcohol during rectification when employed as the agent in azeotropic distillation. They are methyl acetate, dimethyl carbonate, 2-butanone, ethyl propionate, octane, isooctane and 1-octene.

TABLE 3

Effective Azeotropic Distillation Agents Fo Separating 2-Butanol From tert. Amyl Alcohol

| Compounds | Relative Volatility |
|---|---|
| Methyl acetate | 1.8* |
| Dimethyl carbonate | 1.4 |
| 2-Butanone | 1.8* |
| Ethyl propionate | 1.35 |
| Octane | 1.45 |
| Isooctane | 1.3 |
| I-Octene | 1.45 |
| None | 1.2 |

*Reverses the volatility.

THE USEFULNESS OF THE INVENTION

The usefulness of this invention can be demonstrated by referring to the data presented in Tables 1,2 and 3. All of the successful agents show that 2-butanol can be separated from t-amyl alcohol by means of azeotropic distillation in a rectification column and that the ease of separation as measured by relative volatility is considerable.

WORKING EXAMPLES

1. Fifty grams of 2-butanol—t.amyl alcohol mixture and fifty grams of 1-octene were charged to a vapor-liquid equilibrium still and refluxed for two hours. The vapor composition was 74.4% 2-butanol and 25.6% t-amyl alcohol; the liquid composition was 66.7% 2-butanol and 33.3% t-amyl alcohol. This is a relative volatility 2-butanol to t.amyl alcohol of 1.45.

2. Fifty grams of 2-butanol—t-amyl alcohol mixture and fifty grams of methyl acetate were charged to a vapor-liquid equilibrium still and refluxed for two hours. The vapor composition was 26.3% 2-butanol and 73.7% t-amyl alcohol; the liquid composition was 40% 2-butanol and 60% t-amyl alcohol. This is a relative volatility of t-amyl alcohol to 2-butanol of 1.8.

I claim:

1. A method for recovering 2-butanol from a mixture of 2-butanol and t-amyl alcohol which consists essentially of distilling a mixture consisting of 2-butanol and t-amyl alcohol in the presence of an azeotrope forming agent, recovering the 2-butanol and the azeotrope forming agent as overhead product and obtaining the t-amyl alcohol as bottoms product, wherein said azeotrope forming agent consists essentially of one material selected from the group consisting of dimethyl carbonate, ethyl propionate, octane, isooctane and 1-octene.

2. A method for recovering t-amyl alcohol from a mixture of t-amyl alcohol and 2-butanol which consists essentially of distilling a mixture consisting of t-amyl alcohol and 2-butanol in the presence of an azeotrope forming agent, recovering the t-amyl alcohol and the azeotrope forming agent as overhead product and obtaining the 2-butanol as bottoms product, wherein said azeotrope forming agent consists essentially of methyl acetate or 2-butanone.

* * * * *